US008486001B2

United States Patent
Weyant

(10) Patent No.: US 8,486,001 B2
(45) Date of Patent: Jul. 16, 2013

(54) METHOD OF TREATING CAPSULAR CONTRACTURE

(76) Inventor: Tim Weyant, Coral Springs, FL (US)

( * ) Notice: Subject to any disclaimer, the term of this patent is extended or adjusted under 35 U.S.C. 154(b) by 540 days.

(21) Appl. No.: 12/722,944

(22) Filed: Mar. 12, 2010

(65) Prior Publication Data
US 2010/0234772 A1 Sep. 16, 2010

Related U.S. Application Data

(60) Provisional application No. 61/159,478, filed on Mar. 12, 2009.

(51) Int. Cl.
A61B 17/20 (2006.01)

(52) U.S. Cl.
USPC .................................. 604/22; 601/1

(58) Field of Classification Search
CPC ...................................................... A61B 17/20
USPC ............... 128/200.16, 915, 916; 600/437; 602/75; 604/22
See application file for complete search history.

(56) References Cited

U.S. PATENT DOCUMENTS

| 4,806,404 | A | * | 2/1989 | Cascino | 428/40.4 |
| 5,231,977 | A | | 8/1993 | Graston | |
| 5,366,437 | A | | 11/1994 | Graston | |
| 5,441,478 | A | | 8/1995 | Graston | |
| 5,707,346 | A | | 1/1998 | Graston | |
| 6,022,317 | A | * | 2/2000 | Cruanas et al. | 600/439 |
| 6,126,620 | A | | 10/2000 | Graston | |
| 6,540,702 | B1 | * | 4/2003 | Sarango | 601/133 |
| 2003/0212350 | A1 | * | 11/2003 | Tadlock | 601/2 |
| 2004/0015109 | A1 | * | 1/2004 | Villani | 601/133 |
| 2006/0116610 | A1 | | 6/2006 | Hare et al. | |
| 2008/0045876 | A1 | * | 2/2008 | McVicker | 602/76 |

OTHER PUBLICATIONS

J. Planas, M.D., V. Cervelli, M.D., and G. Planas, M.D., Five-Year Experience on Ultrasonic Treatment of Breast Contractures, Aestheic Plastic Surgery, 25:89-93, 2001.
A. Aldo Mottura, M.D. Face Lift Postoperative Recovery—Aestheic Plastic Surgery, 26:172-180, 2002.
Hilton Becker, M.D. and Mark F. Prysi, M.D., Quantitive Assessment of Postoprative Breast Massage, Ideas and Innovations, Mar. 10, 1989.
Hilton Becker, M.D. and Rachelle Springer, A.R.N.P., Prevention of Capsular Contracture, Cosmetic Follow-Up, Jan. 8, 1999.
Peter E. Silversmith, M.D. Ultrasound for Capsualr Contracture of the Breast.—Plastic and Reconstructive Surgery, Mar. 1984—p. 500, vol. 73.
Frank T. Herhahn, M.D., Ultrasound and Capsualr Contracture, Plastic and Reconstructive Surgery—1984, p. 574, vol. 74.
J. Planas, M.D., E. Migliano, MD., J. Wagenfuhr, Jr., MD and S. Castillo, M.D., External Ultrasonic Treatment of capuslar Contracture in Breast Implant Aesthetic Plastic Surgery, 21:395-397, 1977.
Reoperative Plastic Surgey of the Breast, pp. 80-121, Dec. 22, 2005.

* cited by examiner

Primary Examiner — Laura A Bouchelle
Assistant Examiner — Gerald Landry, II
(74) Attorney, Agent, or Firm — Robert M. Schwartz

(57) ABSTRACT

A method of treating and ameliorating capsular contracture having the steps of providing ultrasound at or near the site of a breast implant, providing specific massage and/or physical manipulation the implant site, and providing a compression bandage at the implant site.

16 Claims, 7 Drawing Sheets

SECTION A-A
OF FIG.2

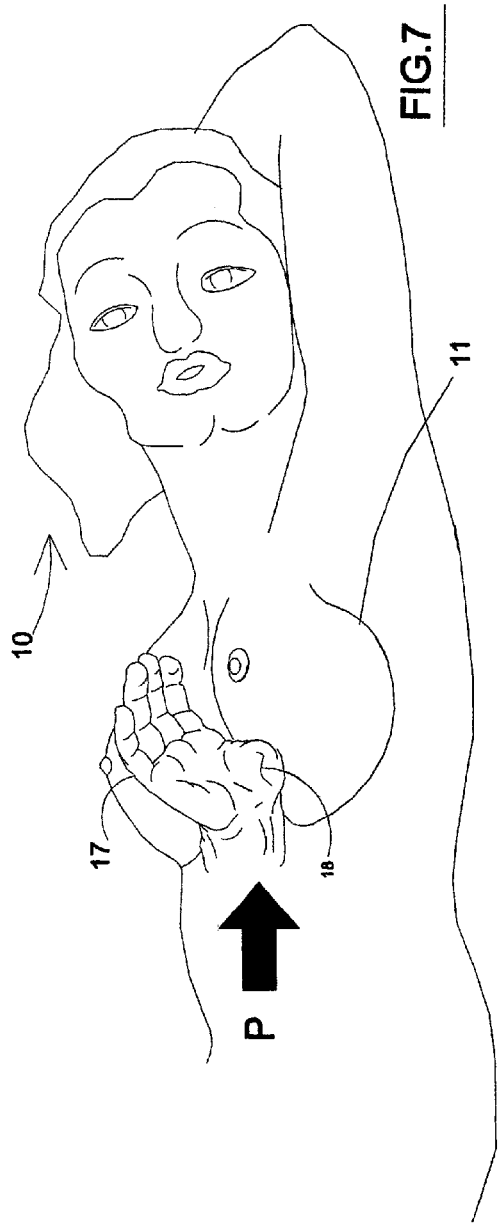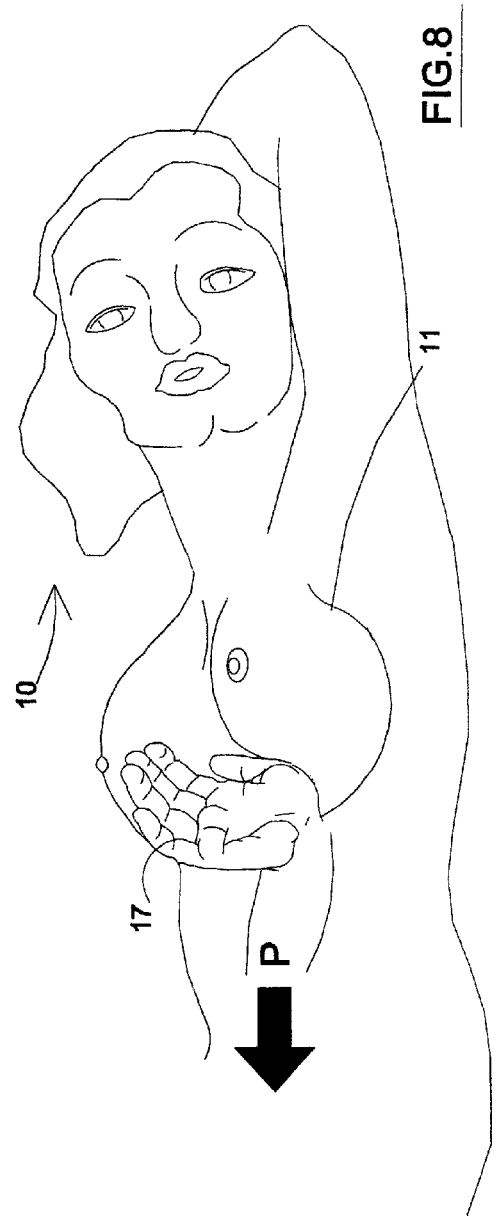

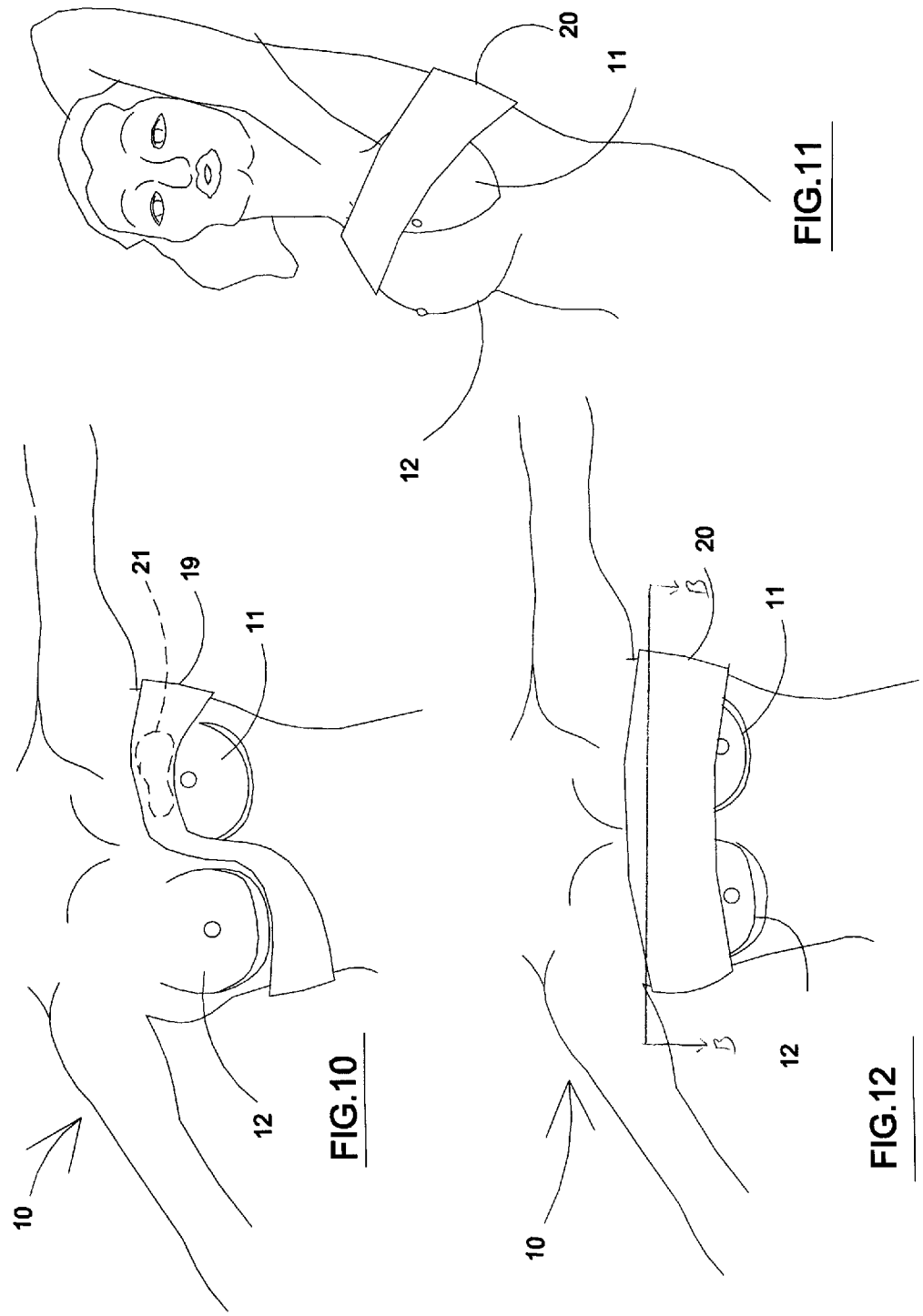

METHOD OF TREATING CAPSULAR CONTRACTURE

INDEX TO RELATED APPLICATIONS

This application claims benefit of U.S. Provisional Patent Application 61/159,478, filed Mar. 12, 2009, the disclosure of which is incorporated herein by reference in its entirety.

BACKGROUND OF THE INVENTION

Capsular contracture (CC) happens when the scar tissue or capsule that normally forms around the implant tightens and squeezes the implant. It can happen to one or both of the implanted breasts.

Capsular contracture may be more common following infection, hematoma, and seroma. However, it is not known for sure why capsular contracture happens. The literature also discusses other factors, such as a textured implant surface and submuscular placement of the implant, which may decrease the capsular contracture rate.

A reoperation may be needed to correct capsular contracture, usually for grade III or IV capsular contracture. The surgical procedures range from removal of the implant capsule tissue with or without replacement of the implant itself. Capsular contracture may happen again after this reoperation.

BRIEF SUMMARY OF THE INVENTION

Capsular Contracture (CC), also commonly renamed Capsular Contraction, is a condition that creates a fibrous "scar" shell around the breast implant in mammals that have had either elective or reconstructive breast augmentations. This scar shell or capsule may cause pain, hardness to the implant, and changes in the shape of the breast producing undesirable results after breast augmentation. CC has been traditionally treated by:

1. Surgically cutting or removing the scar shell
2. Off label medications
3. Mobilization via massage
4. Manipulation externally via a closed capsulotomy or forceful breaking (non-surgically) of the scar capsule by the surgeon.

All the aforementioned statistically may have limited success and come with risks such as re-occurrence, infection, or seroma.

The option of a safe, non-invasive, alternative treatment was warranted.

BRIEF DESCRIPTION OF THE DRAWINGS

FIG. 7 is a side perspective view showing massage technique of the present invention in which the heel of the hand of a masseur is positioned adjacent to the inferior perimeter of the breast and pressure is applied in the superior direction.

FIG. 8 is a side perspective view showing massage technique of the present invention in which the heel of the hand of a masseur is positioned adjacent to the inferior perimeter of the breast and pressure is applied in the inferior direction using the heel of the hand to apply the pressure.

FIG. 10 is a front view showing placement of a compression bandage and positioning of a soft wedge on the superior surface of one breast.

FIG. 11 is a side view showing positioning of a compression bandage over two breasts.

FIG. 12 is a front view showing positioning of a compression bandage over two breasts.

DETAILED DESCRIPTION OF THE PREFERRED EMBODIMENTS

Figure 1:
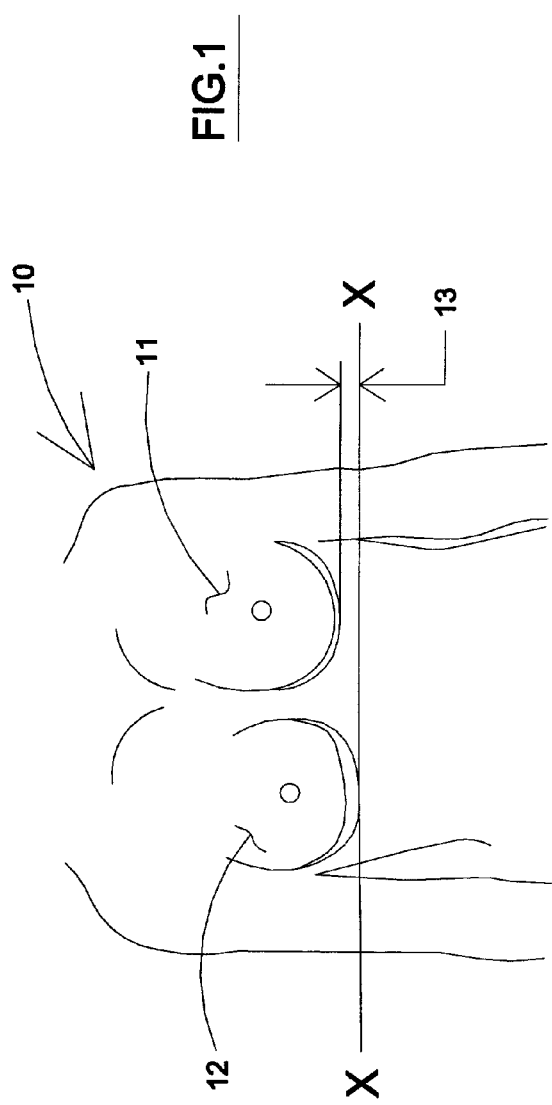
FIG. 1 is a front view of a woman's breasts showing misalignment of the breasts in the frontal plane.

As shown in FIG. 1, a woman 10 has a left breast 11 and a right breast 12. Capsular contracture (CC) often causes breast movement such that the affected breast rests in a higher (i.e. superior) in comparison with a breast that is not affected. In FIG. 1, left breast 11 is above alignment line X-X and is elevated a misalignment distance 13 (distance between arrows) above alignment line X-X.

Figure 2:
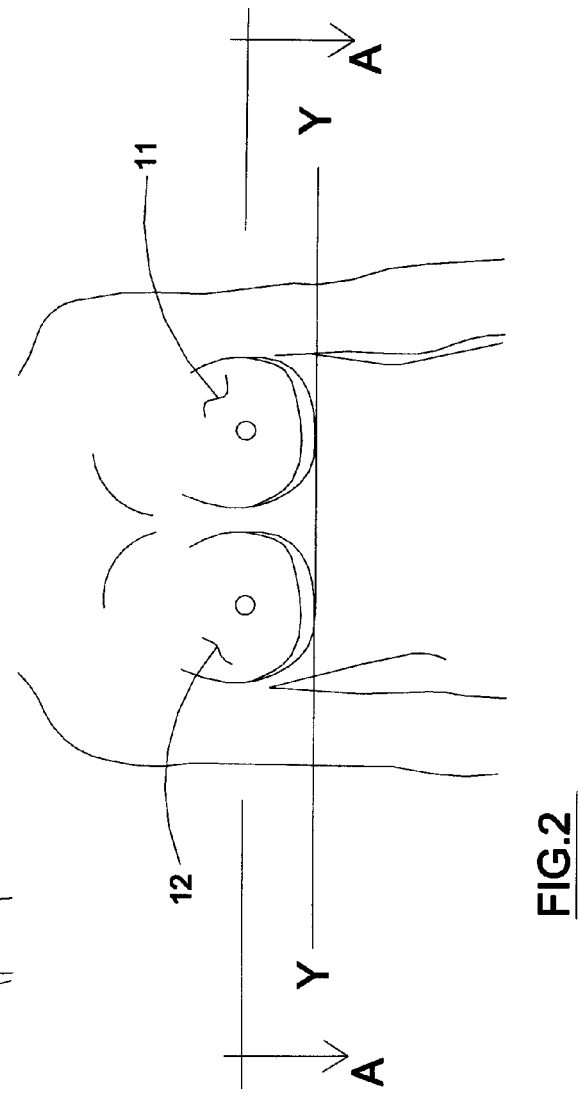
FIG. 2 is a front view of a woman's breasts showing alignment of the breasts in the frontal plane.

FIG. 2 depicts the desired positioning of left breast 11 and right breast 12 each being substantially aligned along realignment line Y-Y.

Figure 3:
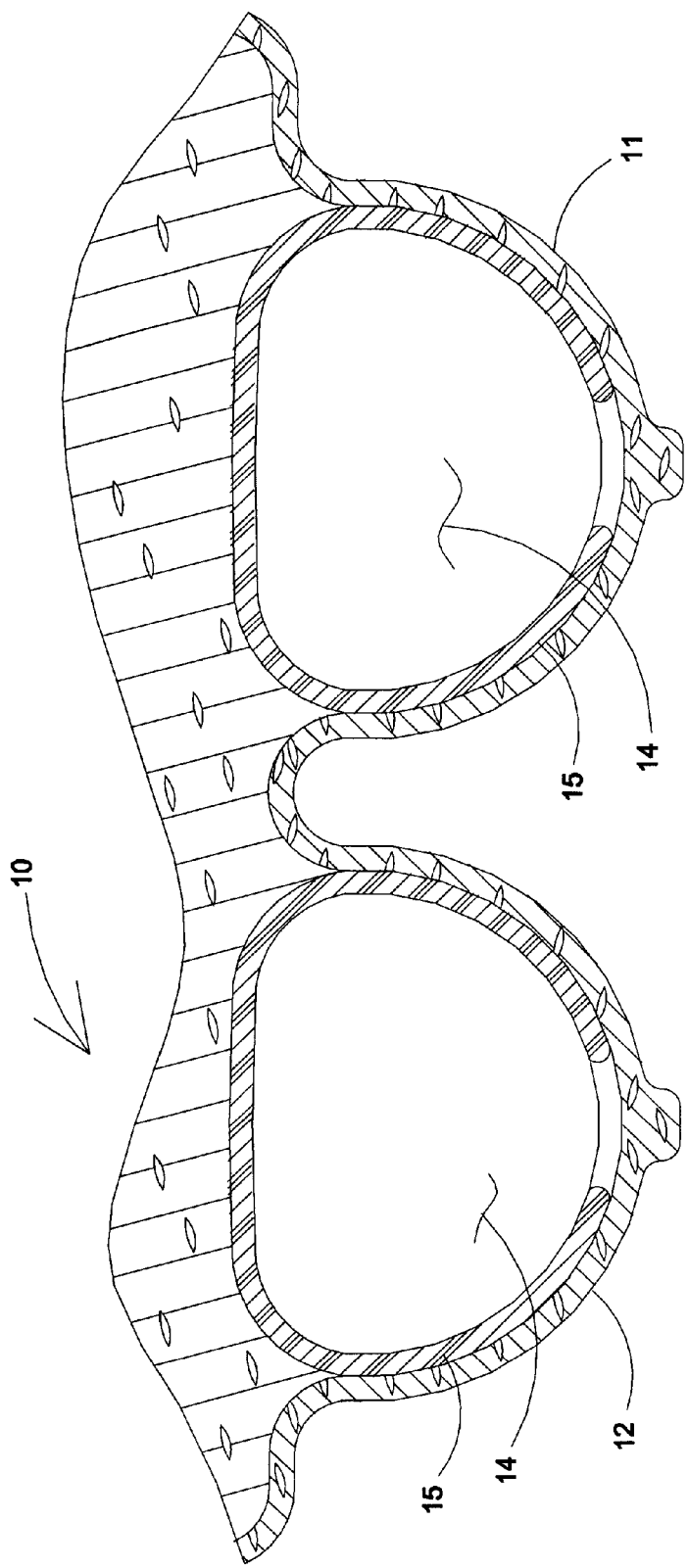
FIG. 3 is a partial cross section from section lines A-A of FIG. 2 showing position of installed breast implants.

FIG. 3 is a cross section along line A-A from FIG. 2 and shows breast implants 14 as are commonly inserted in each of left breast 11 and right breast 12. Each implant is typically surrounded by a breast tissue shell 15. In capsular contracture, shell 15 contracts, squeezes breast implant 14 and misshapes and misaligns either or both of left breast 11 and right breast 12.

The system of the present invention requires ultrasound administration on all sides. This includes superior, inferior, medial, lateral, and central positions of the breast to be treated.

Figure 4:
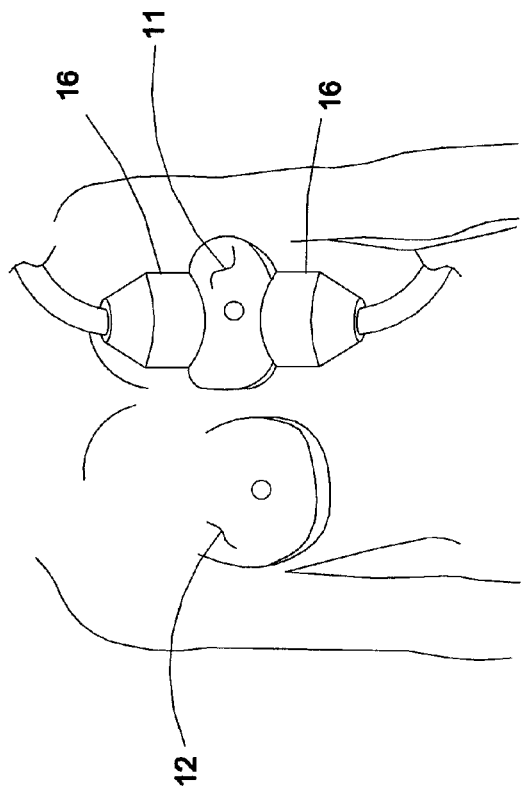
FIG. 4 is a front view of woman's breasts showing placement of ultrasound transducers on the medial and lateral (i.e. inner and outer) portions of one breast.
Figure 6:
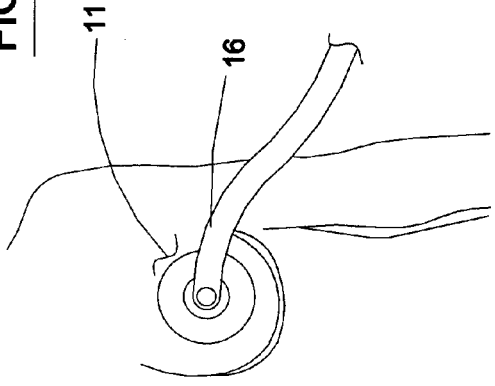
FIG. 6 is a front view of woman's breasts showing placement of ultrasound transducers on the central portion of one breast.
Figure 5:
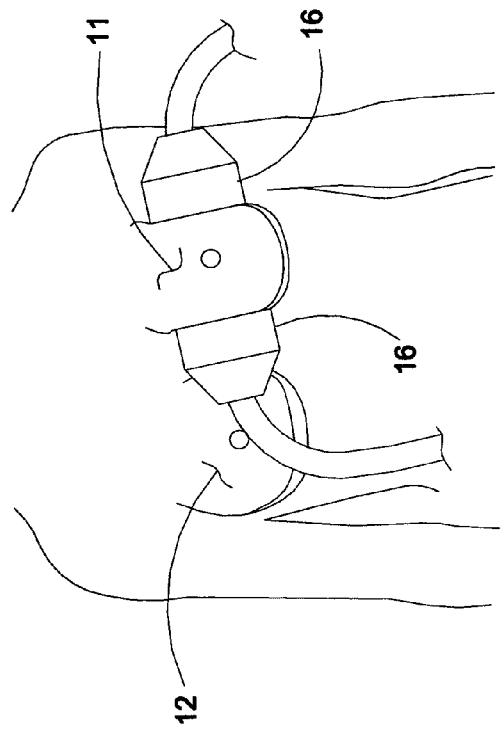
FIG. 5 is a front view of woman's breasts showing placement of ultrasound transducers on the superior and inferior (i.e. upper and lower) portions of one breast.

FIGS. 4-6 demonstrate positioning of ultrasound transducers 16 on breast 11. Although only one breast is depicted in the Figs., it is understood that the present invention is applicable to both breasts. In FIG. 4, transducers 16 are positioned on the medial and lateral surfaces of breast 11. In FIG. 5, transducers 16 are positioned on the superior and inferior surfaces of breast 11. In FIG. 6, a single transducer 16 is positioned on the central surface of breast 11.

FIGS. 7-8 depict a specific massage technique of the present invention. FIG. 8 shows the hand 17 is positioned via placing the heel of the hand (with wrist extended to max extension with fingers straight) on the affected breast (midway between nipple and distal periphery of breast), drawing a skin fold or wrinkle of skin back away from the implant, and then applying a moderate to maximal push in the opposite frontal (coronal) plane on base of implant until capsule end feel is reached in the desired direction and maintaining for a >30 second count. Pressure is then released and repeated to all four sides of the breast (12 o'clock (superior), 3 o'clock (lateral), 6 o'clock (inferior), and 9 o'clock (medial) for a total time of 10-15 minutes.

The motion of FIG. 8 occurs first and is followed by the opposite motion of FIG. 7.

Figure 9:
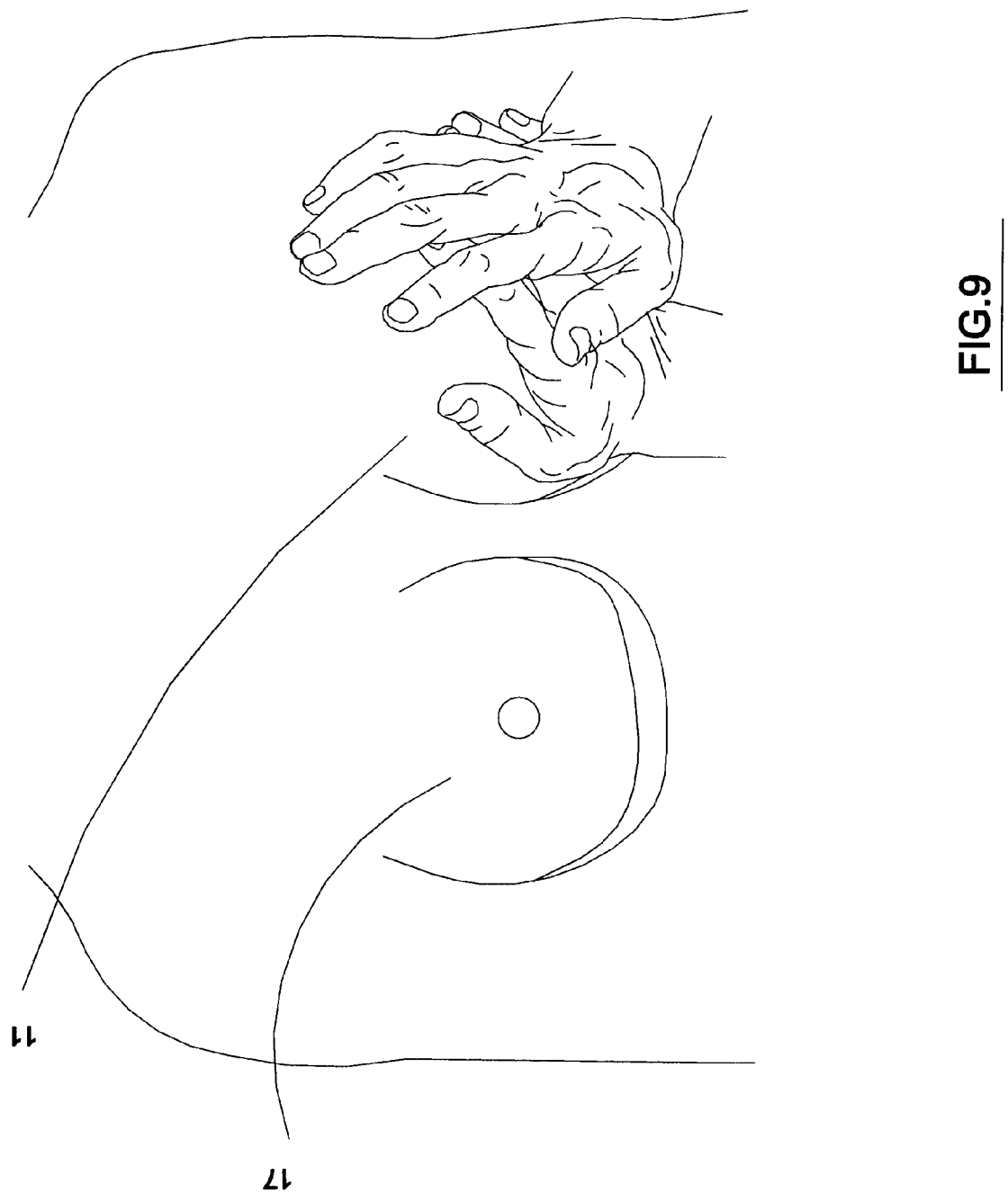
FIG. 9 is a front view showing placement of hands directly on top of the central portion of a breast for administering massage with a downward application of force in a direction substantially perpendicular to the torso of the person receiving the massage.

FIG. 9 shows placement of hands 17 in a central position above breast 11. Downward force is applied in a direction of force substantially perpendicular to torso of body 11 of the person to be treated. Substantially perpendicular is not meant to be limiting to 90 angles. The direction force applied with hands in the central position is similar to direction of force applied in well known CPR techniques.

FIGS. 10-12 show compression bandage techniques according to the present invention. In FIG. 10, bandage 19 is wrapped around the torso of body 10 around the top of breast 11. A kidney bean shaped soft foam positioning device 21 is placed on the superior surface of breast 11. Bandage 19 is placed over device 21. The combination of device 21 and compression bandage 19 urges breast 11 in a lateral and inferior direction in order to realign a misaligned breast.

FIGS. 11 and 12 show compression bandage 20 can be placed over each breast 11 and 12 if each breast 11 and 12 is in need of therapy. Device 21 (not shown in FIGS. 11 and 12) can be placed on the superior surface of either breast or both breasts 11 and 12, as needed.

Figure 13:
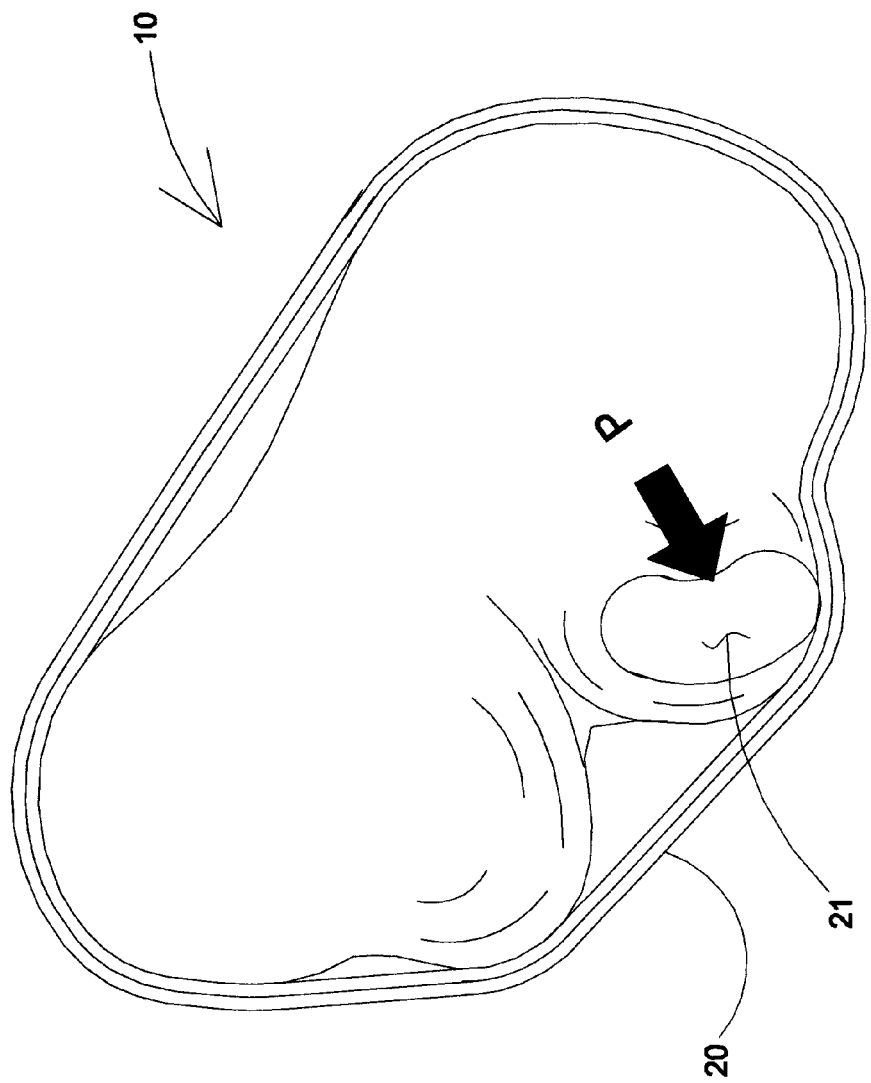
FIG. 13 is a partial top view along section line B-B of FIG. 12.

FIG. 13 is a partial top view along section line B-B of FIG. 12 showing placement of device 21 on the superior surface of breast 11.

A study was performed in developing the method of the present invention.

This study provides an alternative, safe, cost effective treatment option to surgical revision of CC, which may have a high financial cost to the patient and third party insurance payers. Additionally, surgery comes with the risk of infection, hematoma, seroma, and multiple medical complications, as well as a statistically poor success rate with a tendency towards repeated Capsular Contracture. Non-surgical techniques reduce these risks and have been shown to be effective in our study.

The scope of patients that can benefit from a non-surgical treatment option includes all patients worldwide undergoing elective augmentation with implants and those who have suffered breast Cancer and required reconstruction with implants.

Subjects and Methods:

Over 200 patients have been evaluated and treated for CC using the method of the present invention.

This technique incorporates each of:
1.) External Ultrasound therapy
2.) Specific Implant capsule massaging technique and stretching and
3.) Compression bandaging to effectively soften, loosen, and properly position the affected CC implant as a means of avoiding surgical correction.

The present invention has used the technology of external Ultrasound Therapy in conjunction with passive stretching and bandaging (low load prolonged stretch) to treat CC effectively and has established application protocols based on best outcomes.

1.) Ultrasound Therapy

The general rule of Ultrasound application is treatment area should never exceed a size twice the size of the transducer head. As the breast implant was much larger than the overall coverage area (including all 4 transducers) this by default made the Ultrasound application flawed. This does not adequately cover the entire implant surface as it was focal over only 4 small areas. High frequency sound waves have a very focused and directional property, therefore one can also conclude that the only the small area under the transducer was essentially being treated.

The Ultrasound protocol of the present invention, as well as the machine configuration, covers the entire implant, thereby producing a more therapeutically successful result. The present invention incorporates prolonged static stretching (low load static stretch) and massage of the contracted implant capsule that is safer, more effective, and superior to the traumatic nature of closed capsulotomy. Closed Capsulotomy is a forceful squeezing of the breast implant meant to "pop" or "tear" the implant scar capsule. This traumatic technique is not recommended as it can compromise the implant, voids the implant warranty, can create instability in the position of the implant, and can result in repeated contracture.

2.) Implant Capsule Massaging and Stretching:

Implant capsule massages have been a highly debated technique, throughout the history of breast implant procedures, as a means of preventing and treating capsular contracture. Prior studies have concluded that long term follow up data shows no significant difference in capsular contracture rates in relation to massaging the implant after surgery or not. Types of massages vary and differ per surgeons as no universally accepted technique has been adopted or shown to be superior. Some surgeons recommend pinch type massages to displace and maintain pocket patency in avoiding contracture. Some recommend compression exercises via lying on the floor and flattening the implant to stretch and loosen the capsule. Others encourage a more gross pushing and displacing of the implant after surgery or contracture to soften or stretch the capsule. Other surgeons recommend no massage at all especially with textured implants.

The above mentioned massaging can help in the overall treatment of Capsular Contracture but must be more specific in its application per the severity of, and time frame of, contracture. Pinch and compression massages may be beneficial to some extent, but may be limited in advanced Contracture for the following reasons:

1. Self-pinch or displacement massage rendered by the patient may be sub-optimal especially for sub-muscular placement as:
   a.) The pectoralis muscle contracts during self massage due to being tonically controlled for posture in a sitting upright position and the pectoralis contracts as the muscle holds the distal upper extremity while performing the massages. This may limit full displacement during the massage. Being supine and having a significant other or relative perform the massage passively to the patient while relaxed is superior which is what our technique describes.
2. The force and time required to properly displace and create elastic to plastic tissue deformation of the capsule is usually beyond the ability and strength of most patients. This is why most patients report only a short term or temporary resolution to firmness but no sustained long-term improvement in softness or implant positional distortions with the above techniques. This is because most implant massages are only held for a few seconds (3-5 seconds). The present invention has discovered a particular massage technique, being performed statically, is held for about 30 seconds or longer, significantly improves the contracture and allows the breast to return from a contracted position to a natural position. The present invention has shown that a stretch creates permanent elongation when held statically (>30 seconds) over a long period of time versus balistically over a short period of time (quick pinch done many times)

3. The skin over the implant must be drawn back and slack given so that pressure during the massage is directed at the implant versus force lost to stretching of the skin. The message technique of the present invention provides a specific method to create the desired slack and increase pressure on the implant.

3.) Compression Bandaging:

1.1. A surgeon issued compression bandage is typically prescribed after surgery to provide a downward force on both breasts, aid stability and reduce pain, and help with recovery of the patient. This is usually a single layer white elastic wrap that has Velcro to secure it and wraps one time around the patient's torso and breasts. When capsular contracture occurs, the implant capsule contracts usually creating a Superiorly>Medially>Anteriorly mal-positioned implant relative to the uninvolved side or natural position. The "Capsular Pattern" of implant Capsular Contracture refers to the altered position of the breast due to CC. When this "Capsular Pattern" occurs, it is important to use a compression bandaging system that effectively "pushes" and stretches the implant capsule to allow the implant to return to its intended position. In order to do this, a more advanced system of bandage was needed to be used. The previously used white bandage method is replaced in the present invention with a multi layered 2-way short stretch compression bandage typically used for Venous insufficiency or Lymphedema patients. Unlike the previous white bandage applied by surgeons, the 2-way bandage wraps multiple times around the patients body and affected breast. This was superior to the surgeon applied white strap as it allows for a more natural flow of lymphatic and venous flow under the garment, had a less "tourniquet" affect with more even pressure distribution, provided more compression to the implant, and was more aesthetically appealing as it was thinner and less noticeable under clothing.

Prior discussions relating to treatment fail to evaluate duration and adjustment of how the bandage is wrapped, how long it is applied, and the level of compression to produce effective results. In order to create a steering or redirecting of the implant, the present invention incorporates a kidney bean shaped soft wedge 21 under bandage 20 to increase pressure and "steerability" of the implant. The pressure is applied to push the breast in an inferior and lateral direction to as to assist the return to a natural position.

Testing the Method of the present invention.

Subjects and Methods:

Over 200 patients with CC (elective and reconstructive) have been treated using the combined inventive system having: 1.) Ultrasound therapy 2.) Implant massaging and stretching and 3.) Compression bandaging to effectively soften, loosen, and properly position the affected CC implant.

1.) Ultrasound Therapy a. The goal of Ultrasound is to use its thermal and nonthermal properties of loosening, softening, and realigning collagen and scar tissue in the contracted breast implant capsule.

Ultrasound parameters: 0.1-0.31 W/cm2, pulsed, 50% duty cycle, 3.3 MHz settings have been used based on the type of surgery and patient response to the Ultrasound. Breast reconstruction patients typically use 0.1-0.2 w/cm2 due to the shallow nature of the implant and minimal native fat and tissue covering the shallow implant while elective breast augmentation with implants that lay below the pectoralis muscle is deeper and require 0.2-0.31 W/cm2 for deeper penetration.

Transducer(s): 1 and/or 2 are applied to entire surface of the breast ensuring all of the external breast(s) surface is covered over total treatment. The transducer(s) is left in place for minimum 2 minutes-maximum 10 minutes per segment of breast treated. The transducers 16 are then moved until all areas of breast have been covered with Ultrasound and treatment time is based on severity of contracture and patient response to treatment (pain, heat, discomfort, redness).

2.) Implant Massaging and Stretching:

a. The goal is to stretch the internal breast implant scar capsule on all sides to effectively loosen the scar capsule and return the breast (breast implant) to normal softness, shape, and reduce pain.

i. Utilizing the hands of the treating therapist or significant other, manual compression is applied to the affected implant capsule while not stretching the superficial skin. This is done via placing the heel of the hand (with wrist extended to max extension with fingers straight) on the affected breast (midway between nipple and distal periphery of breast), drawing a skin fold or wrinkle of skin back away from the implant, and applying a moderate to maximal push in the frontal (coronal) plane until capsule end feel is reached in the desired direction and maintaining for a >30 second count. Pressure is then released and repeated to all four sides of the breast (12 o'clock (superior), 3 o'clock (lateral), 6 o'clock (inferior), and 9 o'clock (medial) for a total time of 10-15 minutes.

ii. Utilizing the hands of the treating therapist, moderate to maximal pressure is applied via the therapists hand (palm flat) centrally to breast (nipple region) for >30 seconds with the patient in supine position to effectively flatten and create compression of the implant without the use of Ultrasound.

Total time of manual implant massaging and compression per breast is 10-15 minutes. This is repeated 3 times a day. More or less time may be prescribed per breast as per CC grade and severity of CC.

3.) Compression Bandaging:

a. The purpose of the compression bandage is to provide a low load, static stretch to the scar capsule of the implant to accomplish two goals.

1. Soften and stretch the contracted capsule.
2. Properly position the mal-positioned implant.

i. A short stretch 2-way compression bandage is applied circumferentially around the patient's body and over the breast(s) either superiorly, centrally, medially, or laterally per the desired direction of the stretch and compression. Example: If the implant has been more laterally displaced then the bandage is wrapped toward the lateral side of breast to push it medially. If the implant has been more superiorly displaced then the bandage is applied to the superior surface of the breast creating an inferior push. A kidney bean wedge (soft padding) may be added under the bandage to focus compression and direction desired to the implant(s). Cloth tape is used to secure the bandage. The patient is instructed to wear the bandage 23 hours a day minus massage time until desired softness, position, and shape are achieved. The proper use of bandage, as well as risks and benefits are discussed.

Compression bandaging was measured and applied in the range of 1500-3000 Pa (Pascal, wherein 1 Pascal is known as equal to one Newton per square meter ($N/m^2$) and the Newton is recognized as being 1 $kg \cdot m \cdot s^{-2}$).

Techniques have changed over time and evolved to the method of the current invention as a day protocol and methods as described below for the treatment of CC. These changes over the past 3-year period are represented in Table 1 below.

Table 1:
1.) External Ultrasound Therapy.
   Year 1: Unit A: Mobile transducer wand (Standard therapeutic) Continuous Ultrasound 2.0 W/Cm2, 5 cm2 sound head, ×8 minutes to spot areas (3-4 average) of implant hardness or firmness.
   Size of ultrasound area covered: Ultrasound 5 cm2 coverage area via mobile wand.
   (Total time at focal implant spot treatment area—10 cm2 for 2 min average.)
   Year 2: Unit B: Stationary transducer applicator Continuous Ultrasound at 1.0-2.0 W/cm2, 17 cm2 sound head to entire implant surface×16-22 minutes.
   Size of ultrasound area covered: 17 cm2 coverage area via stationary transducer.
   (Total time per segment to cover entire implant surface-17 cm2 for 2 minutes.)
   Year 3: Unit C: Stationary transducer applicator at 0.1-0.31 W/Cm2, 2 Transducers each being 65 cm2 sound head to entire implant surface×16-18 minutes
   Size of ultrasound area covered: 65 cm2 coverage area via stationary transducer
   (Total time per segment to cover entire implant surface—65 cm2 for 2-10 minutes.)
   Summary of Changes: Improved Results:
1. Lowering the overall Wattage/cm2 from 2 to 0.31
2. Increasing the amount of surface area/time spent over a fixed area from 10 cm2@ 2 minutes to 65 cm2@ 2-10 minutes.
3. Utilizing a computer controlled sound head that electronically controls the application of ultrasound versus a mobile wand transducer, which increases the chance for human error.

2.) Implant Capsule Massaging and Stretching.
   Year 1: General myofascial release massage and chest stretching to peri-implant region.
   Year 2: Specific focused implant pocket mobilization for 5 sec hold.
   Year 3: Specific focused implant pocket mobilization for 5 sec hold and added manual implant compression and sustained pocket excursion techniques for >30 second hold time.
   Summary of changes: We have seen improved results by increasing focused static stretch time to the implant capsule and type of implant mobilization.

3.) Compression Bandaging.
   Year 1: No bandage used.
   Year 2: Physician ordered min. compression strength single layer white bandage over both breasts worn to patient tolerance per day.
   Year 3: Custom multi-layered short-stretch 2-way compression increase strength bandage applied per mal-positioning of the patients breast implant worn for 23 hrs a day.
   Summary of changes: We have seen improved results by increasing static stretch time and strength of compression bandaging to the implant capsule.

Methods:
21 patients with CC (16 elective and 5 reconstructive augmentations with implants) were randomly selected for this study and have been analyzed after being treated using the Aspen Rehabilitation Technique (ART). In order to test the results of the ART, two grading systems were used to measure the two most common disorders associated with CC:

Common disorders of CC:
a.) Breast Softness
b.) Ideal breast position/shape

Grading Systems Used:
1. Patient Subjective Report: Patients were asked at the termination of formal treatment to give a subjective score of improvement from their initial visit to their final visit using a (0-10) score based on both a.) Breast Softness (See Table 1) and b.) Ideal breast position/shape

TABLE 1

Patient satisfaction with breast softness before and after undergoing ART (treatment of the present invention.

| Rating | Before ART (Number of Patients) | After ART (Number of Patients) |
|---|---|---|
| 0 | 4 | 0 |
| 1 | 3 | 0 |
| 2 | 1 | 0 |
| 3 | 3 | 0 |
| 4 | 1 | 1 |
| 5 | 0 | 0 |
| 6 | 0 | 0 |
| 7 | 0 | 0 |
| 8 | 0 | 2 |
| 9 | 0 | 4 |
| 10 | 0 | 6 |

2. Clinician Objective Evaluation: At the termination of treatment, the clinician rated the improvement scores based on objective measure of a.) and b.):
   a.) Breast Softness using the Baker Grading system (See below Table 2)

TABLE 2

Baker grade before and after undergoing ART (4 = worst, 1-best)

| Rating | Before ART (Number of Patients) | After ART (Number of Patients) |
|---|---|---|
| 4 | 3 | 0 |
| 3 | 11 | 1 |
| 2 | 6 | 6 |
| 1 | 1 | 14 |

Baker Grading System
Grade I: Breast looks and feels normal
Grade II: Breast feels a little firm but looks normal
Grade III: Breast is more firm and is visually distorted (shape change or mal-positioned)
Grade IV: Breast is hard and greatly distorted in shape and position b.) Ideal breast position/shape via superior/inferior linear measurement of mal-positioning of the CC implant in comparison to the uninvolved or contralateral breast at initial and final visit (See table 3).

Table 3: Linear Measurement

TABLE 3

Asymmetry of breast position before and after undergoing ART (vertical distance between the inferior aspect of the breast with the CC versus the uninvolved and/or contralateral breast)

| Distance in millimeters | Before ART (Number of Patients) | After ART (Number of Patients) |
|---|---|---|
| 0 | 1 | 10 |
| 1 | 2 | 3 |
| 2 | 1 | 4 |
| 3 | 0 | 3 |

TABLE 3-continued

Asymmetry of breast position before and after undergoing ART (vertical distance between the inferior aspect of the breast with the CC versus the uninvolved and/or contralateral breast)

| Distance in millimeters | Before ART (Number of Patients) | After ART (Number of Patients) |
|---|---|---|
| 4 | 1 | 0 |
| 5 | 0 | 0 |
| 6 | 0 | 0 |
| 7 | 1 | 0 |
| 8 | 0 | 0 |
| 9 | 1 | 0 |
| 10 | 1 | 0 |
| 11 | 1 | 0 |
| 12 | 2 | 0 |
| 13 | 2 | 0 |
| 14 | 0 | 0 |
| 15 | 0 | 0 |
| 16 | 2 | 0 |
| 17 | 0 | 0 |
| 18 | 2 | 0 |
| 19 | 0 | 0 |
| 20 | 0 | 0 |
| 21 | 1 | 0 |
| 22 | 1 | 0 |
| 23 | 0 | 0 |
| 24 | 0 | 0 |
| 25 | 1 | 0 |

Results:

Patient satisfaction with breast softness before undergoing ART ranged from 0 to 4, with a mean of 1.55 (SD=1.44). Patient satisfaction with breast softness after undergoing ART ranged from 4 to 10, with a mean of 8.85 (SD=1.56). This is a mean improvement of 7.3 (SD+1.73).

Baker grades before undergoing ART ranged from 1 to 4, with a mean of 2.76 (SD=0.75). Baker Grades after undergoing ART ranged from 1 to 3, with a mean of 1.38 (SD=0.58). This is an average decrease of 1.38 grades.

Asymmetry of breast position before undergoing ART ranged from 4 to 25 millimeters (mm), with a mean of 11.54 (SD=7.23).

Asymmetry of breast position after undergoing ART ranged from 0 to 3 mm., with a mean of 0.93 (SD=1.13). This is a mean decrease of 10.60 mm (SD=6.10), or 92%

Patient perception of overall improvement resulting from ART ranged from 6 to 10, with a mean of 8.45 (SD+1.44).

Overall, patient's perception of overall improvement from ART was 8.45 on a 10-point scale.

There were no negative side effects reported.

Discussion and Conclusion

Current options for treatment of Capsular Contracture traditionally involve the surgical revision of the breast capsule via open capsulotomy or capsulectomy. These surgical approaches may come with the risk of repeated CC, native breast tissue loss, infection, hematoma, or seroma. The above-mentioned techniques, being applied externally, limit risk to the patient and provide safe alternative methods to surgical revision. The researchers believe the following study on ART shows great potential for non-surgical options both prophylactically and post onset of CC and opens the door for further research on these and other non-surgical techniques.

Limitations to this research study include inter and intra-rater reliability scoring, improved objective measurement systems, limited data collection on patient subjective scoring, patient compliance with instructed ART guidelines and recommended treatments as prescribed, advanced stage fibrosis of CC (Baker grade 4) prior to starting the treatment, and the need for long term follow up studies on long term results.

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention.

I claim:

1. A method of treating and ameliorating capsular contracture having the steps of: (a) administering external ultrasound therapy at or near the capsule surrounding an implant site of a breast implant by at least one ultrasound transducer pulsed at about 0.1-0.31 W/cm$^2$ with ultrasound pulses for about 2-10 minutes; (b) providing massage and/or physical manipulation at said implant site; (c) providing a compression bandage at said implant site.

2. The method of claim 1 wherein said ultrasound therapy is provided by at least one ultrasound. transducer pulsed at about 0.1-0.2 W/cm$^2$.

3. The method of claim 1 wherein said ultrasound is provided over substantially all of the capsule surrounding a breast implant.

4. The method of claim 1 wherein ultrasound is applied on a portion of an external breast surface selected from the group consisting of the medial surface portion, the lateral surface portion, the superior surface portion, the inferior surface portion and the central nipple surface portion.

5. The method of claim 1, wherein said massage/physical manipulation is performed by: (a) a person other than the patient placing a heel of the person's hand having a wrist extended to maximum extension with fingers straight on the affected breast, said placement being midway between nipple and distal periphery of the breast; (b) drawing a skin fold or wrinkle of skin back away from said breast implant; (c) applying a moderate to maximal push in the frontal or coronal plane until the end of the capsule is reached in the desired direction; and (d) maintaining said maximal push for about 30 seconds or more.

6. The method of claim 1 wherein said massage and/or physical manipulation is carried out continuously over a period. of about 15 minutes.

7. The method of claim 1 wherein said massage and/or physical manipulation is carried out up to three times per day.

8. The method of claim 1 wherein said massage is performed on each of the medial, lateral, superior, and inferior sides of the breast.

9. The method of claim 1 wherein said compression bandage is applied with a short stretch 2-way compression bandage circumferentially around the patient's body and over the breast either superiorly, centrally, medially, or laterally per the desired direction. of the stretch and compression.

10. The method of claim 1 wherein said compression bandage is applied for up to about 23 hours per day.

11. The method of claim 1 wherein said compression bandage is applied to impart about 150-2500 Pa of force on said breast in which said compression bandage is applied.

12. The method of claim 1 wherein ultrasound is applied by a first ultrasound transducer on the superior portions of the breast and by a second ultrasound transducer on the inferior portions of the breast.

13. The method of claim 1 wherein ultrasound is applied by said first ultrasound transducer on the lateral portions of the breast and by said second ultrasound transducer on the medial portions of the breast.

14. The method of claim 12 wherein ultrasound is applied from about 4-8 minutes on the top of the breast by applying ultrasound from one of said first ultrasound transducer or said second ultrasound transducer to tie central nipple portion of the breast.

15. The method of claim 1 wherein said ultrasound therapy is provided by at least one ultrasound transducer, said ultrasound transducer having a size greater than about 17 cm$^2$.

16. A method of massaging breasts for the treatment of capsular contracture having the steps of: (a) administering external ultrasound therapy at or near the capsule surrounding an implant site of a breast implant by at least one ultrasound transducer pulsed at about 0.1-0.31 W/cm$^2$ with ultrasound pulses for about 2-10 minutes; (b) providing massage performed by a person other than the patient placing a heel of the person's hand having wrist extended to max extension with fingers straight on the affected breast, said placement being midway between nipple and distal periphery of breast; (c) drawing a skin fold or wrinkle of skin back away from said implant; and (d) applying a moderate to maximal push in the frontal or coronal plane until capsule end feel is reached in the desired direction.

\* \* \* \* \*